United States Patent
Kunitomi et al.

(10) Patent No.: US 11,781,190 B2
(45) Date of Patent: Oct. 10, 2023

(54) DISCOVERY OF BIOLOGICAL SIGNATURES OF OPTIMIZED SENSITIVITY AND SPECIFICITY

(71) Applicant: International Business Machines Corporation, Armonk, NY (US)

(72) Inventors: Mark Kunitomi, San Francisco, CA (US); Daniel Waddington, Morgan Hill, CA (US)

(73) Assignee: International Business Machines Corporation, Armonk, NY (US)

( * ) Notice: Subject to any disclaimer, the term of this patent is extended or adjusted under 35 U.S.C. 154(b) by 375 days.

(21) Appl. No.: 16/987,329

(22) Filed: Aug. 6, 2020

(65) Prior Publication Data
US 2022/0042114 A1    Feb. 10, 2022

(51) Int. Cl.
*G01N 33/48*    (2006.01)
*C12Q 1/6888*   (2018.01)
*G16B 5/00*     (2019.01)
*G16B 30/00*    (2019.01)
*G16B 50/00*    (2019.01)

(52) U.S. Cl.
CPC ............. *C12Q 1/6888* (2013.01); *G16B 5/00* (2019.02); *G16B 30/00* (2019.02); *G16B 50/00* (2019.02)

(58) Field of Classification Search
None
See application file for complete search history.

(56) References Cited

U.S. PATENT DOCUMENTS

| | | |
|---|---|---|
| 2018/0365375 A1 | 12/2018 | Flygare et al. |
| 2019/0130998 A1 | 5/2019 | van Rooyen et al. |
| 2019/0237162 A1 | 8/2019 | Ye |
| 2019/0318807 A1 | 10/2019 | O'Hara et al. |

FOREIGN PATENT DOCUMENTS

CN    106681688 A    5/2017

OTHER PUBLICATIONS

Baker and Langmead, Dashing: fast and accurate genomic distances with HyperLogLog, Genome Biology 20 (265):1-12, 2019.
Kaplinski et al., GenomeTester4: a toolkit for performing basic set operations—union, intersection and complement on k-mer lists, GigaScience 4(58):1-8 (2015).
Koslicki et al., Improving Min Hash via the Containment Index with Applications to Metagenomic Analysis, bioRxiv 2017 (pp. 1-13), available at https://doi.org/10.1101/184150.
Muthu et al., Studies on Antimicrobial Susceptibility Pattern of *Salmonella* Isolates from Chennai, India, International Journal of Pharma and Bio Sciences 2(2):B435-B442 (2011).
Ondov et al., Mash: fast genome and metagenome distance estimation using MinHash, Genome Biology 17(132):1-14 (2016).
Ondov et al., Mash Screen: high-throughput sequence containment estimation for genome discovery, Genome Biology 20(232):1-13 (2019).
Ounit et al., Clark: fast and accurate classification of metagenomic and genomic sequences using discriminative k-mers, BMC Genomics 16(236):1-13 (2015).
Solis-Reyes et al., An open-source k-mer based machine learning tool for fast and accurate subtyping of HIV-1 genomes, bioRxiv 2018 (pp. 1-21), available at https://doi.org/10.1101/362780.
Grace Period Disclosure: Waddington et al., Evaluation of Intel 3D-Xpoint NVDIMM Technology for Memory-Intensive Genomic Workloads, MEMSYS '19 (2019, pp. 1-11), available at https://doi.org/10.1145/3357526.3357528.
Wang et al., Identifying Group-Specific Sequences for Microbial Communities Using Long k-mer Sequence Signatures, Frontiers in Microbiology 9(872):1-18 (2018).
Wood and Salzberg, Kraken: ultrafast metagenomic sequence classification using exact alignments, Genome Biology 15(R46):1-12 (2014).

*Primary Examiner* — Anna Skibinsky
(74) *Attorney, Agent, or Firm* — Karen Canaan; CanaanLaw, P.C.

(57) ABSTRACT

A bioinformatics method is provided for identifying candidate biological sequences, such as DNA, RNA, and proteins, with high sensitivity and specificity for application in procedures such as PCR and gene and protein sequencing. The method involves categorizing a collection of biological sequences within an out-group and an in-group, identifying the intersection between the in-group and the out-group, the union of the out-group, and a relative complement of sequences that are members of the in-group, but not the out-group. A biological signature for a species of interest with high sensitivity and specificity will be a member of the relative complement that has an out-group frequency of zero.

12 Claims, 2 Drawing Sheets

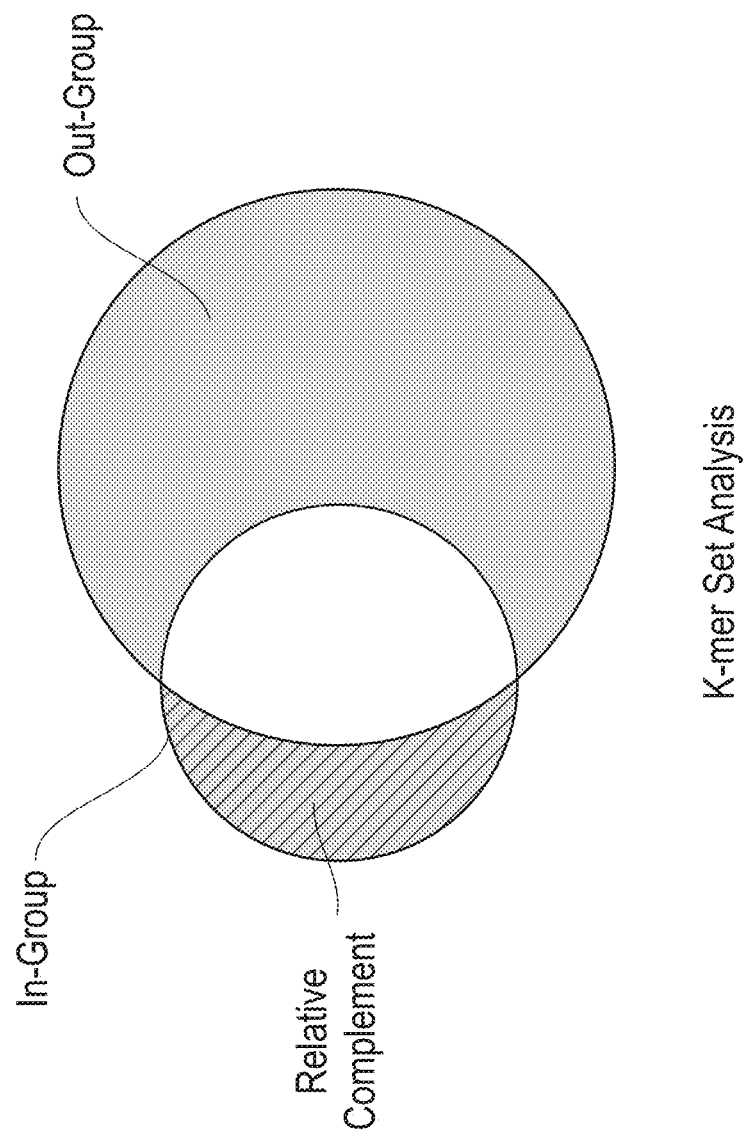

DISCOVERY OF BIOLOGICAL SIGNATURES OF OPTIMIZED SENSITIVITY AND SPECIFICITY

STATEMENT REGARDING PRIOR DISCLOSURES BY THE JOINT INVENTORS

The following disclosure is submitted under 35 U.S.C. § 102(b)(1)(A): DISCLOSURE: Waddington et al., Evaluation of Intel 3D-Xpoint NVDIMM Technology for Memory-Intensive Genomic Workloads, MEMSYS '19 (2019, pp. 1-11).

TECHNICAL FIELD

The present invention relates generally to bioinformatics, and more specifically to in silico methods for the identification of biological signatures from within background samples.

BACKGROUND OF THE INVENTION

Bacteria represent one of the greatest threats to public and food safety. Rapid assessment of the proper treatment for a bacterial infection has drastic effects on patient outcome. For example, patients with typhoid fever that do not receive timely and appropriate treatment are estimated to have a 30% mortality rate, whereas that mortality rate is reduced to just 0.5% for patients that receive timely and appropriate treatment.

Nucleic acid-based detection systems, such as the Polymerase Chain Reaction (PCR), are the primary class of rapid diagnostic tools to determine bacterial identity. Such tests have a wide range of applications, including detecting pathogens in food ingredients and products, characterizing environmental microbiota, and diagnosing infectious diseases. The success of such assays depends on the ability of the test to identify sequences (i.e., signatures) that properly differentiate between the target organism(s) and the sample background, the latter of which includes all other organisms potentially present in the sample. A major limitation of nucleic acid-based detection systems is that prior information about target sequence and off-target sequences is necessary in order to generate specificity of the method. Further, the prior information must be representative of the diversity of the larger population of organisms in the environment.

Bacterial genetic diversity has led to bacterial inhabitance in almost every known habitable niche on earth. This wide-ranging diversity causes difficulties in the ability to detect, combat, and even categorize bacteria; however, the availability of accessible and cost-effective high-throughput sequencing is currently increasing the number of sequenced bacterial genomes. As of November 2017, the number of sequenced bacterial species available in GENBANK® (US Dept of Health and Human Services, Bethesda, Md., USA) is in excess of 100,000. Given the large number of bacterial species that will continue to be sequenced, there is a need in the art for methods to access information from the sequences that can reduce the risk of harm on human and animal populations from detrimental bacterial contamination.

SUMMARY OF THE INVENTION

The present invention overcomes the skill in the art by providing in silico methods for the identification of biological signatures from within background samples.

In one aspect, the present invention relates to a method of identifying a biological signature of a species of interest comprising: (a) establishing an out-group by (i) extracting contigs from at least one-member sequence, and (ii) inserting k-mers for at least one species of the at least one-member sequence; (b) establishing an in-group by removing k-mer entries from the out-group that have a frequency count not equal to the member sequences; and (c) establishing a relative complement to the in-group and the out-group by iterating over each k-mer in the out-group and scanning the in-group for out-group k-mers, wherein the biological signature of the species of interest comprises k-mers that have an out-group frequency at or near zero.

In another aspect, the present invention relates to a method of identifying a biological signature of a species of interest comprising: (a) initiating a query comprising a collection of biological sequences from at least one genome; (b) establishing an out-group hash table by (i) extracting contigs from all of the member sequences of the at least one genome, and (ii) inserting k-mers for member sequences from at least one species of the at least one genome; (c) establishing an in-group hash table by (i) establishing an in-group intersection by removing k-mer entries that have a frequency count not equal to all of the member sequences of the at least one genome; and (d) establishing a relative complement to the in-group and the out-group hash tables by incrementing in-group k-mer frequency values by out-group k-mer frequency count, wherein the relative complement includes in-group k-mers that are not found in the out-group and the biological signature of the species of interest comprises k-mers in the relative complement that have an out-group frequency at or near zero.

In a further aspect, the present invention relates to a method of identifying a biological signature of a species of interest comprising: (a) establishing an out-group by (i) extracting contigs from at least one-member sequence, and (ii) inserting k-mers for species associated with the at least one-member sequence; (b) establishing an in-group by removing k-mer entries from the out-group that have a frequency count not equal to all of the member sequences of the at least one genome; (c) establishing a relative complement to the in-group and the out-group by removing all k-mers from the in-group that occur in the out-group; and (d) assembling k-mers from the relative complement into overlapping contigs, wherein the overlapping contigs comprise the biological signature for the single species.

In other aspects and embodiments, the relative complement k-mers are assembled into contigs.

In further aspects and embodiments, the contigs overlap by one base.

In other aspects and embodiments, the contigs overlap by all but one base.

In further aspects and embodiments, any out-group k-mers in the relative complement are scrubbed by incrementing a frequency value of the in-group k-mers by a frequency count of the out-group k-mers.

In other aspects and embodiments, the relative complement is scrubbed of k-mers having a frequency count>an established epsilon value.

In further aspects and embodiments, the epsilon value is 0.1-1.0.

In other aspects and embodiments, the biological signature of the species of interest is selected from the group consisting of DNA sequences, RNA sequences, amino acid sequences, and protein sequences.

In further aspects and embodiments, the at least one-member sequence is selected from the group consisting of genomes, genes, proteins, domains, and combinations thereof.

In other aspects and embodiments, the at least one-member sequence is a bacterial genome and the at least one species is a bacterial species.

Additional aspects and/or embodiments of the invention will be provided, without limitation, in the detailed description of the invention that is set forth below.

BRIEF DESCRIPTION OF THE DRAWINGS

FIG. 2 is diagram showing the relationship between an in-group, an out-group, and a relative complement.

DETAILED DESCRIPTION OF THE INVENTION

Figure 1:
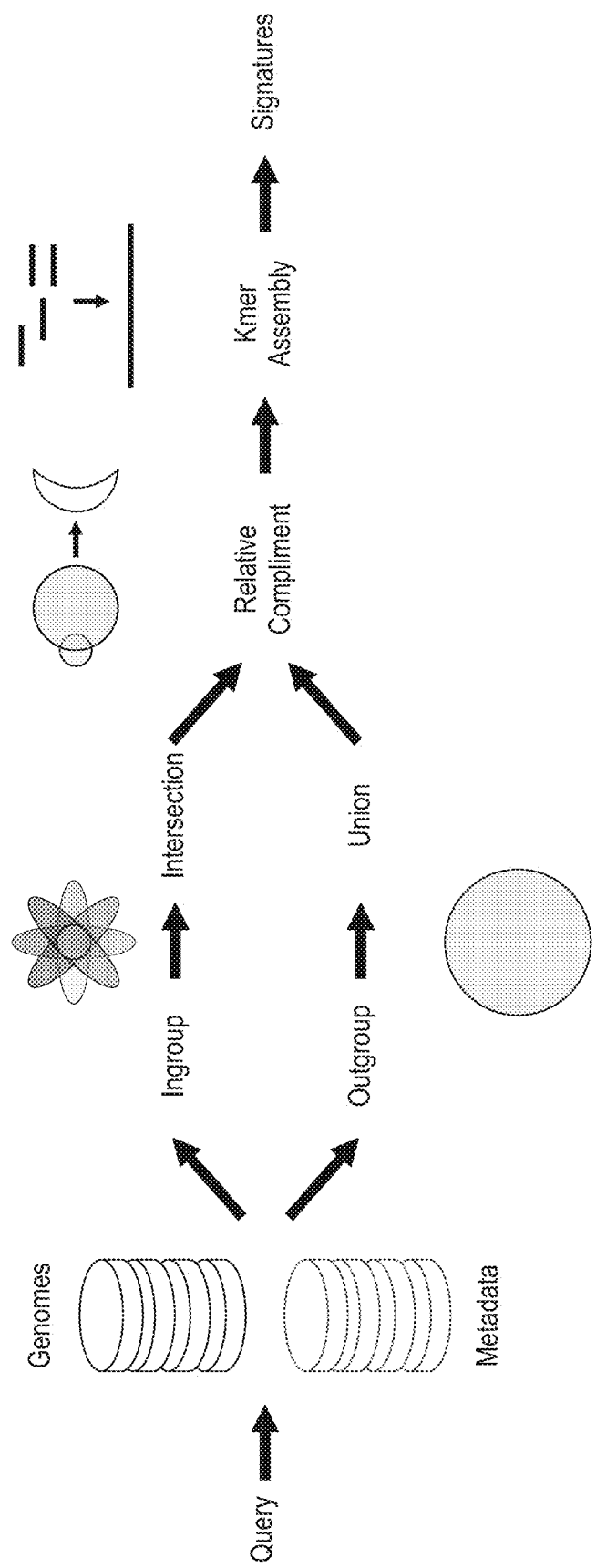
FIG. 1 is a schematic diagram of the logic process described herein.

Set forth below is a description of what are currently believed to be preferred aspects and/or embodiments of the claimed invention. Any alternates or modifications in function, purpose, or structure are intended to be covered by the appended claims. As used in this specification and the appended claims, the singular forms "a," "an," and "the" include plural referents unless the context clearly dictates otherwise. The terms "comprise," "comprised," "comprises," and/or "comprising," as used in the specification and appended claims, specify the presence of the expressly recited components, elements, features, and/or steps, but do not preclude the presence or addition of one or more other components, elements, features, and/or steps.

As used herein, the term "sequence" or "biological sequence" refers to a nucleotide sequence of DNA and RNA and/or an amino acid sequence of proteins. Within the context of the present invention, biological sequences include genes, contigs, sequences and subsequences from any genome, the latter including, without limitation, human genomes, bacterial genomes, viral genomes, prokaryotic genomes, and eukaryotic genomes.

As used herein, the term "metadata" refers to the descriptions and sampling sites and habitats that provide the context for sequence information. Examples of metadata include, without limitation, geographical location of the sample, features of the environment of the sample, chemical data from the sample, method of sampling, sample size, sample preparation.

As used herein, the term "member" refers to a genus selected from one or more of a genome, gene, protein, domain, and/or other sequence of biological information. The term "member sequence" and "member sequences" refers to one or more sequences that comprise a particular genus. Within each member will be individual species with one or more sequences specific to those species.

As used herein, the term "signature" and "biological signature" refers to one or more biological sequences that differentiate an individual species from a sample background (i.e., the one or more member sequences of the background).

As used herein, the term "contig" refers to a set of overlapping sequences that represent a contiguous sequence from a sequence assembly, the latter being known in the art as a sequence that is reconstructed from the aligning and merging of DNA fragments from a longer DNA sequence.

As used herein, the term "k-mer" refers to an individual from a set of all the possible substrings of length k that are contained in a string or set of strings. In bioinformatics, k-mers are subsequences of length k contained within a biological sequence. Within the context of computational genomics and sequence analysis, k-mers are composed of nucleotides (e.g., A, C, T, G, U, and N (any nucleotide) or amino acids (e.g., the 20 amino acids that make up proteins). Using nucleotides as an example, the term k-mer refers to all of a sequence's subsequences of length k, such that the sequence AGAT would have four monomers (A, G, A, T), three 2-mers (AG, GA, AT), and one 4-mer (AGAT). A sequence of length L will have L−k+1 k-mers and $n^k$ total possible k-mers, where n is the number of possible monomers (e.g., four nucleotides in the case of DNA or RNA and 20 amino acids in the case of proteins).

As used herein, the terms "in-group" and "out-group" refer to groups containing biological signatures. FIG. 2 shows an interaction between an in-group and an out-group. For purposes of illustration, examples of out-groups will include broad bacterial genera, such as, for example, *Salmonella, Escherichia,* and *Pseudomonas*. Examples of in-groups will include species found within the out-group, such as, for example, *Salmonella* Virchow, *Salmonella enterca, Escherichia coli,* and *Pseudomonas aemginosa*. Within the context of the present invention, an in-group will include members that are true positives or false negatives while an out-group will include members that are true negatives or false positives.

The "accuracy," or the degree that a material measured is similar to its true value, is calculated according to Formula (1):

$$(P+TN)/(TP+FP+FN+TN), \quad (1)$$

where TP is a true positive, TN is a true negative, FP is a false positive, and FN is a false negative.

The "sensitivity," or true positive (TP) rate, is a percentage of members within an in-group that contain a signature. Sensitivity is calculated according to Formula (2):

$$(TP/(TP+FN)). \quad (2)$$

The "specificity," or true negative (TN) rate, is a percentage of members outside of an in-group (i.e., member of an out-group) that does not contain a signature. Specificity is calculated according to Formula (3):

$$(TN/(TN+FP)). \quad (3)$$

The term "union" and its mathematical symbol U generally refers to all members of a set. Within the context of the present invention, U refers to the out-group k-mers. The union is filtered by member count number 1 representing a single member embodied to X (i.e., the number of members) representing all of the members as determined by the user.

The term "intersection" and its mathematical symbol n generally refers to an intersection between two sets. Within the context of the present invention, n refers to the in-group k-mers that are also in the out-group (shown in FIG. 2). The intersection is computed by removing the k-mer entries that have a frequency count below a user defined number of percentages of in-group members.

As used herein, the term "relative complement" refers to all k-mers in the in-group that are not intersected with the out-group. FIG. 2 provides a representation of how the relative complement relates to the in-group and the out-group. Within the context of the present invention, k-mers in a relative complement represent sensitive and specific biological signatures.

For the following mathematical symbols, the sets will be one or more sets of contigs.

The mathematical symbol ∈ is used in its traditional sense to reference an element of a set. Within the context of the present invention, the elements will be contigs and the set will be a set of contigs.

The mathematical symbol ∅ is used in its traditional sense to reference an empty set.

Formulas (1), (2), and (3) are used to calculate the effectiveness of the procedures described herein.

Described herein are in silico methods to determine the maximal specificity and sensitivity of a plurality of k-mers from an in-group and an out-group and redefining the k-mers as contiguous sequences (contigs). With reference to FIG. 1, the method begins with a query, which is a collection of biological sequences. The biological sequences are defined as in-group or an out-group based on the sequence metadata. The intersection of the k-mers of the in-group and the union of the k-mers of the out-group are developed and the relative compliment is taken from the in-group intersection and the out-group union. FIG. 2 shows such a k-mer set analysis. The relative compliment between two sets of k-mers is computed by removing all k-mers from the in-group set if they occur in the out-group set. The relative compliment represents a set of k-mers with a sensitivity score equal to the percentage of members within the in-group that contain the k-mer as calculated by dividing number of true positives by the sum of true positive and false negatives (TP/(TP+FN)) and specificity score equal to the percentage of members, outside of the in-group that does not contain the k-mer as calculated by dividing true negatives by the sum of true negatives plus false positives (TN/(TN+FP)). From the relative compliment, k-mers are assembled into longer contigs where they overlap by all but one base. The relative compliment can then be filtered by a user defined threshold for the sensitivity and specificity scores. The remaining k-mers are then examined to determine if they can be joined to create a longer contigs. Each contig will consist of unique k-mers, so contigs will not overlap by more than one k−1 base. Contigs end when there is a branch or dead-end in the k-mer graph.

Following is an exemplary application of the method to a bacterial genomic sequence. The exemplary genome g is an unordered set of contigs and a contig c is an ordered sequence of bases b:

$$g=\{c_0,c_1,c_2, \ldots c_n\},$$

$$c_i=(b_0,b_1,b_2, \ldots b_m):b \in \{A,C,T,G,N\}.$$

The group of bacteria to identify is the in-group $I_G$ and the group of bacteria that should not be mistakenly identified is the out-group $O_G$, which are shown by Formulas (4) and (5), respectively, where $I_G \cap O_G = \emptyset$:

$$I_G=\{g:g \in \mathbb{U}\}, \quad (4)$$

$$O_G=\{g:g \in \mathbb{U}\}, \quad (5)$$

The set of contigs in the in-group and the outgroup is shown by Formulas (6) and (7), respectively:

$$I_C=U_{g \in I_G}\{c:c \in g\}, \quad (6)$$

$$O_C=U_{g \in O_G}\{c:c \in g\}. \quad (7)$$

The k-mer k, which is a (sliding window) substring of the contig c of length L (nominally 100), is calculated according to Formula (8):

$$k_i^L=\text{canonical\_choice}((b_i,b_{i+1},b_{i+2}, \ldots b_{i+L-1}),(b'_{i+L-1},b'_{i+L-2}, \ldots b'_i)), \quad (8)$$

where i≥0 and I<|c|−L.

The set of k-mers K for contig c of length L is calculated according to Formula (9):

$$K^L(c)=\cup_{i=0}^{|c|-L}k_i^L \quad (9)$$

The in-group k-mers intersection $I_{kL}$ is calculated according to Formula (10):

$$I_{kL}=\cap_{c \in I_c}K^L(c). \quad (10)$$

The out-group set of k-mers $O_{kL}$ is calculated according to Formula (11):

$$OI_{kL}=\cup_{c \in O_c}K^L(c). \quad (11)$$

The foregoing formulas may be used to develop k-mer sets with no false positives (Objective 1) or with minimal false positives (Objective 2).

Objective 1: Exact match objective (no false-positives). Find set of k-mers M:

$$M=\{k:k \in I_{kL} \wedge k \notin O_{kL}\}$$

or $$M=I_{kL}-O_{kL}$$

Frequency count of k-mer k in set s is given by:

$$f:(k,s) \to \mathbb{Z}+ \text{ where } f(k,s)=|\{k:k \in s\}|$$

Objective 2: Exact match objective (minimize false-positives). Find set of k-mers M:

$$M = \{k : k \in I_{kL}\} \text{ where } \sum_{k \in M} f(k, O_{kL}) \text{ is minimized}$$

Example 1 describes the application of objectives 1 and 2 to identify relative complement DNA sequences. Example 2 describes the application of the procedure in Example 1 to identify specific and sensitive PCR primers derived from the relative complement of the *Salmonella* out-group and the *Salmonella* Virchow in-group. The PCR-based bacterial detection solution of Example 2 was successfully able to determine the presence of the *Salmonella virchov* species from within five bacterial samples without triggering, as a false-positive, other member species of the *Salmonella* genus.

The descriptions of the various aspects and/or embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the aspects and/or embodiments, the practical application or technical improvement over technologies found in the marketplace, or to enable others of ordinary skill in the art to understand the aspects and/or embodiments disclosed herein.

Experimental

The following examples are set forth to provide those of ordinary skill in the art with a complete disclosure of how to make and use the aspects and embodiments of the invention as set forth herein. In the examples that follow, data was obtained from the public NCBI (National Center for Biotechnology Information GenBank (https://www.ncbi.nlm.nih.gov/genbank/) repository and IBM internally acquired bacterial reference data. The experiments were conducted on OPTANE® (Intel Corporation, Santa Clara, Calif., USA) Data-Centric Persistent Memory (PMDC). In Example 1, an XOR digital logic gate is used. With an XOR gate, a true output results if one, and only one, of the inputs to the gate is true (1 or HIGIH). If no inputs are false or both are true, a false output results (0 or LOW). XOR represents the inequality function, i.e., the output is true if the inputs are not alike, otherwise the output is false.

Example 1

Sequence Alignment

The relative complement of a DNA sequence was determined by analyzing in-group intersection and out-group union of DNA sequences.

FASTA file preparation. A FASTA DNA and sequence alignment software package was used for file preparation. Each zipped FASTA file was unzipped and each contig was converted to a 3-bit raw (bit packed) format. The following procedure was followed:
1. Encode bases with:
   A 001
   C 010
   G 100
   T 111
   N 011
   U 110
2. Apply XOR 0x7 to derive complement. This encoding maintains alphabetical ordering with numerical ordering.
3. Write each contig to log-storage (append only) and add metadata to database (filename, record index).

In-group Intersection. Parallelizing genomes across threads (i.e., each genome is processed by exactly one thread) ensures k-mer frequency is only incremented once per genome (maintained in thread local storage, TLS).
1. Create hash table with key=hash_of_k-mer and value=genome_occurrences. Hash of k-mer is 64-bit hash of 8-bit-per-base DNA string.
2. Load 3-bit data and convert into in-memory 8-bit form. 8-bit form allows sliding window extraction. Canonical form is determined (and marked) during k-mer construction.
3. Perform sliding window extraction on all contigs for all genomes. Increment genome_occurrences only once for each new genome.
4. Insert k-mer into hash table—materialize canonical form (perform reversal if need). Dual-sliding window approach can be used to avoid reversals at a cost of transient memory footprint.
5. After all k-mers have been loaded, remove the k-mer entries that have a frequency count not equal total number of members (i.e., this will produce the intersection).
6. Reset frequency counts to 0.

Out-group Union. Same steps as for in-group intersection, but no entries are removed resulting in the union (leave frequency count).

Relative Complement (Candidate Identification)
1. Iterate over each k-mer in the out-group hash table. Check if any of the iterated out-group k-mers exists in the in-group hash table. If there are iterated out-group k-mers in the in-group, increment the in-group k-mer frequency value by the out-group k-mer frequency count.
2. Optionally periodically scrub the in-group hash table of k-mers where frequency count is >than an established epsilon, such as, for example 0.1-1.0.
3. After all out-group k-mers have been processed, scan in-group hash table for k-mers with lowest frequency. Frequency=0 is a perfect candidate (i.e., the relative complement only includes true positive sequences).

Example 2

K-Mer Analysis for PCR Primers

A production genomic workload was used to test a PCR-based bacterial detection solution by identifying a small primer substring of nucleotides (a k-mer where k=100) that can be readily amplified by PCR and used as the basis for identification. The purpose of the bacterial identification was to determine if a sample of bacteria belongs to a given in-group and does not belong to others in the broader out-group. For the test, the in-group was the serovar *Salmonella virchov* and the out-group included the broader species *Salmonella*.

The analysis required the identification of an in-group intersection k-mer set and an out-group union k-mer set; both sets being unique k-mers. From the two sets, the relative complement analysis of Example 1 was performed in order to identify k-mers in the in-group that were not in the out-group (i.e., the relevant complement). The relative complement k-mers became the primer candidates and were taken further into the primer design process. Aside from PCR identification, this type of k-mer based analysis is also applicable for comparison of genomic sequences that are subject to highly-changing mutations, such as found in bacteria.

The genomic datasets used for the experiment as well as the unique k-mers derived (the in-group intersection k-mers and the out-group union k-mers) are shown in Table 1.

TABLE 1

| No. | Dataset | Genome Count | Base-Pairs (billions B) | Unique k-mers (millions M or billions B) |
| --- | --- | --- | --- | --- |
| 1 | Salmonella | 48200 | 232 B | 605.9M |
| 2 | Salmonella Virchow | 336 | 1.58 B | 25.7M |
| 3 | Salmonella Enterica | 13014 | 60.6 B | 923.3M |
| 4 | Salmonella Enterica + Escherichia Coli | 47635 | 237.4 B | 2.59 B |
| 5 | Salmonella Enterica + Escherichia Coli + Pseudomonas Aeruginosa | 52538 | 269.5 B | 2.88 B |
| 6 | GenBank (Ref Seq Complete) | 7641 | 32.0 B | 14.5 B |

We claim:

1. A computer-implemented method of identifying a biological signature of a species of interest from a query comprising a collection of biological sequences, comprising:
   (a) establishing an out-group by (i) extracting contigs from at least one-member sequence of the collection of biological sequences, and (ii) entering k-mers for at least one species of the at least one-member sequence into an out-group hash table;
   (b) establishing an in-group by removing k-mers from the out-group hash table that have a frequency count not equal to the at least one-member sequence of the collection of biological sequences and entering the remaining k-mers from the out-group hash table into an in-group hash table; and
   (c) establishing a relative complement to the in-group and out-group by computationally iterating over each k-mer in the out-group hash table to eliminate out-group k-mers that intersect with the k-mers in the in-group hash table, wherein the relative complement represents the biological signature of the species of interest and comprises in-group k-mers that have an out-group frequency count at or near zero.

2. The computer-implemented method of claim 1, wherein the relative complement k-mers at (c) are assembled into contigs.

3. The computer-implemented method of claim 2, wherein the contigs overlap by one base.

4. The computer-implemented method of claim 2, wherein the contigs overlap by all but one base.

5. The computer-implemented method of claim 1, wherein any out-group k-mers in the relative complement are scrubbed by incrementing a frequency value of the in-group k-mers by a frequency count of the out-group k-mers.

6. The computer-implemented method of claim 1, wherein the biological signature of the species of interest is selected from the group consisting of DNA sequences, RNA sequences, amino acid sequences, and protein sequences.

7. The computer-implemented method of claim 1, wherein the at least one-member sequence is selected from the group consisting of genomes, genes, proteins, domains, and combinations thereof.

8. The computer-implemented method of claim 1, wherein the at least one-member sequence is a bacterial genome and the at least one species is a bacterial species.

9. The computer-implemented method of claim 1, wherein each k-mer in the out-group and in-group hash tables is a 64-bit hash of an 8-bit-per-base DNA string.

10. The computer-implemented method of claim 1, wherein the in-group includes members that are true-positives (TP) or false negatives (FN) and the out-group includes members that are true negatives (TN) or false positives (FP).

11. The computer-implemented method of claim 10, wherein a true positive rate is calculated according to the following formula:

$$(TP/(TP+FN)).$$

12. The computer-implemented method of claim 10, wherein a true negative rate is calculated according to the following formula:

$$(TN/(TN+FP)).$$

* * * * *